US011229366B2

(12) United States Patent
Maki et al.

(10) Patent No.: US 11,229,366 B2
(45) Date of Patent: Jan. 25, 2022

(54) CARDIAC FUNCTION MEASUREMENT DEVICE, CARDIAC FUNCTION MEASUREMENT METHOD, AND CARDIAC FUNCTION MEASURING PROGRAM (71) Applicant: TERUMO KABUSHIKI KAISHA, Tokyo (JP)

(72) Inventors: Shin Maki, Ebina (JP); Tomoki Utsugida, Machida (JP)

(73) Assignee: TERUMO KABISHIKI KAISHA, Tokyo (JP)

( * ) Notice: Subject to any disclaimer, the term of this patent is extended or adjusted under 35 U.S.C. 154(b) by 516 days.

(21) Appl. No.: 16/134,396

(22) Filed: Sep. 18, 2018

(65) Prior Publication Data
US 2019/0014991 A1 Jan. 17, 2019

Related U.S. Application Data (63) Continuation of application No. PCT/JP2017/009785, filed on Mar. 10, 2017.

(30) Foreign Application Priority Data

Mar. 18, 2016 (JP) .............................. JP2016-055197

(51) Int. Cl.
A61B 5/00 (2006.01)
A61B 5/02 (2006.01)
(Continued)

(52) U.S. Cl.
CPC ........ *A61B 5/02007* (2013.01); *A61B 5/0059* (2013.01); *A61B 5/1079* (2013.01);
(Continued)

(58) Field of Classification Search
CPC .............. A61B 2576/02; A61B 5/0059; A61B 5/02007; A61B 5/1079; A61B 5/742;
(Continued)

(56) References Cited

U.S. PATENT DOCUMENTS

2008/0200784 A1 8/2008 Cheng
2010/0215223 A1* 8/2010 Abe ................... G06K 9/00899
382/115

(Continued)

FOREIGN PATENT DOCUMENTS

JP 2005069918 A 3/2005
JP 2009028058 A 2/2009
(Continued)

OTHER PUBLICATIONS

International Search Report (PCT/ISA/210) dated May 23, 2017, by the Japanese Patent Office as the International Searching Authority for International Application No. PCT/JP2017/009785.
(Continued)

*Primary Examiner* — Mark D Remaly
(74) *Attorney, Agent, or Firm* — Buchanan Ingersoll & Rooney PC (57) ABSTRACT A cardiac function measuring apparatus, a cardiac function measuring method, and a cardiac function measuring program capable of monitoring cardiac functions are disclosed. The cardiac function measuring apparatus for measuring data for evaluating cardiac functions includes an irradiation unit for irradiating a jugular with light, an imaging unit configured to acquire image data of the jugular, and a vein discriminating part configured to discriminate a shape of the jugular vein in the acquired image data and to calculate a shape complexity level indicating complexity in the shape of the jugular.

10 Claims, 7 Drawing Sheets (51) Int. Cl.
 G06T 7/60 (2017.01)
 A61B 5/107 (2006.01)
(52) U.S. Cl.
 CPC ............... *G06T 7/60* (2013.01); *A61B 5/742* (2013.01); *A61B 5/746* (2013.01); *A61B 5/7475* (2013.01); *A61B 2576/02* (2013.01); *G06T 2207/30101* (2013.01)
(58) Field of Classification Search
 CPC ............ A61B 5/746; A61B 5/7475; G06T 2207/30101; G06T 7/60; G16H 30/40
 See application file for complete search history.

(56) References Cited

U.S. PATENT DOCUMENTS

| | | | | |
|---|---|---|---|---|
| 2012/0218568 | A1* | 8/2012 | Yorimoto | B41J 29/38 358/1.5 |
| 2014/0323831 | A1* | 10/2014 | Sato | A61B 5/489 600/301 |
| 2015/0251074 | A1* | 9/2015 | Ahmed | A61B 5/02416 700/91 |

FOREIGN PATENT DOCUMENTS

| | | |
|---|---|---|
| JP | 2010517711 A | 5/2010 |
| JP | 2011178799 A | 9/2011 |
| JP | 2011229615 A | 11/2011 |
| JP | 2014064951 A | 4/2014 |

OTHER PUBLICATIONS

Written Opinion (PCT/ISA/237) dated May 23, 2017, by the Japanese Patent Office as the International Searching Authority for International Application No. PCT/JP2017/009785.

An English Translation of the International Search Report (Form PCT/ISA/210) and the Written Opinion of the International Searching Authority (Form PCT/ISA/237) dated May 23, 2017, by the Japanese Patent Office in corresponding International Application No. PCT/JP2017/009785. (6 pages).

\* cited by examiner

CARDIAC FUNCTION MEASUREMENT DEVICE, CARDIAC FUNCTION MEASUREMENT METHOD, AND CARDIAC FUNCTION MEASURING PROGRAM

CROSS-REFERENCES TO RELATED APPLICATIONS

This application is a continuation of International Application No. PCT/JP2017/009785 filed on Mar. 10, 2017, which claims priority to Japanese Application No. 2016-055197 filed on Mar. 18, 2016, the entire contents of both of which is incorporated herein by reference.

FIELD OF THE INVENTION

The present disclosure generally relates to a cardiac function measuring apparatus, a cardiac function measuring method, and a cardiac function measuring program configured to measure data for evaluating cardiac functions.

BACKGROUND DISCUSSION

When a cardiac output is lowered due to a decrease of cardiac action, a biological mechanism for maintaining the cardiac output can be activated to help prevent or reduce deterioration of the output. However, this can result in a burden to various part of a body, and consequently, symptoms may appear. Cardiac arrest is not a disease name, and means a "physical state arrived as a result of insufficient cardiac action" as described above.

When cardiac arrest occurs, a pumping function of the heart is deteriorated, and thus the heart cannot deliver a sufficient amount of blood. Therefore, blood failed to be delivered from the heart is accumulated in an internal organ immediately before the heart in a circulatory system and symptoms may appear. In a case of left cardiac arrest, symptoms may appear in a pulmonary circulation, and in the case of right cardiac arrest, symptoms may appear in a systemic circulation. Blood returning from the entire body flows to a right side of the heart. However, the right cardiac arrest blocks the blood flow to the right side of the heart and results in hemostasis in the systemic circulation. As a result, symptoms such as distention of jugular veins, hepatic enlargement, ascites fluid, and edema may appear.

Therefore, various apparatuses configured to detect cardiac arrest are known. For example, JP-A-2014-64951 describes an apparatus configured to detect cardiac arrest by monitoring breathing via a cannula inserted into the nose or a mask placed on the mouth of the person.

However, it can be difficult to gain consciousness of an indication of cardiac arrest. Therefore, people become aware of the indication only when acute exacerbations such as cardiac infarction have occurred in many cases. However, since earlier detection obviously makes it easier to take measures, long-term monitoring with a reduced burden to a person being measured is desired.

However, the apparatus described in JP-A-2014-64951 having a relatively large size can present difficulties in wearing and measuring on a daily basis and can impose a relative burden to the person being measured.

SUMMARY

A cardiac function measuring apparatus, a cardiac function measuring method, and a cardiac function measuring program allowing a long-term monitoring of the heart are disclosed having a reduced burden to a person being measured.

A cardiac function measuring apparatus is disclosed, which is configured to measure data for evaluating cardiac functions including: an irradiation unit configured to irradiate a jugular with light; an imaging unit configured to acquire image data of the jugular; and a vein discriminating part configured to discriminate a shape of a jugular vein in the acquired image data and to calculate a shape complexity level indicating complexity in the shape of the jugular vein.

A cardiac function measuring method is disclosed, which measures data for evaluating cardiac functions includes: irradiating a jugular with light; acquiring image data of the jugular irradiated with light; discriminating a shape of a jugular vein in the acquired image data; and calculating a shape complexity level indicating complexity in a shape of the discriminated jugular vein discriminated.

A cardiac function measuring program stored in a non-transitory, tangible computer readable recording medium configured to be executed by a computer is disclosed for measuring data for evaluating cardiac functions including: acquiring image data of a jugular from an imaging unit capable of imaging the jugular; discriminating a shape of a jugular vein in the acquired image data; and calculating a shape complexity level indicating complexity in shape of the discriminated jugular vein.

The cardiac function measuring apparatus, the cardiac function measuring method, and the cardiac function measuring program configured as described above achieve monitoring of shape complexity level of a jugular vein as an indication of deterioration of cardiac functions according to complexity in shape by using image data of the jugular. The cardiac function measuring apparatus may have a compact size and provides a relatively easy-to-measure configuration and may achieve long-term monitoring with relatively less burden to a person being measured.

DETAILED DESCRIPTION

Exemplary embodiments of the disclosure will be described with reference to the drawings below. Note that dimensional ratios of the drawings may be exaggerated and thus may be different from actual ratios for the sake of convenience of description.

A cardiac function measuring apparatus 10 according to an exemplary embodiment of the disclosure is an apparatus configured to monitor complexity level in shape of a jugular vein in a jugular from a body surface. The jugular vein expands (is enlarged) and assumes a complex shape due to deterioration of functions of the right ventricle. As used herein the term "complex shape" is intended to include dimensions, sizes, angles and the like of various parts, being not constant and varying. Therefore, observing the complexity level of the jugular vein enables determination of deterioration of the functions of the right side of the heart (right cardiac arrest). The jugular vein includes an external jugular vein and an internal jugular vein. Therefore, the jugular vein to be observed by the cardiac function measuring apparatus 10 may include the external jugular vein or the internal jugular vein. The cardiac function measuring apparatus 10 is used on the daily basis by a person being measured by him/herself and is capable of monitoring a change of a cardiac status on a relatively long-term basis. The cardiac function measuring apparatus 10 may also be used for a purpose of short-term monitoring such as determining presence or absence of cardiac arrest for a couple of days under the instruction of a doctor to achieve diagnosis with a relatively higher degree of accuracy than a short time observation at the hospital.

As illustrated in FIGS. 1 to 4, the cardiac function measuring apparatus 10 includes an imaging unit 20 configured to take an image, a brightness detection unit 30 configured to detect brightness, an irradiation unit 80 configured to irradiate a subject with light, a memory unit 40 configured to store various data, a control unit 50, an input unit 70, a display unit 60, and a housing 90. The housing 90 is configured to house the imaging unit 20, the brightness detection unit 30, the irradiation unit 80, the memory unit 40, the control unit 50, the input unit 70, and the display unit 60. The control unit 50 and the memory unit 40 constitute a computer that executes a program. Therefore, the operation of the cardiac function measuring apparatus 10 may be executed by a program.

Figure 2A:
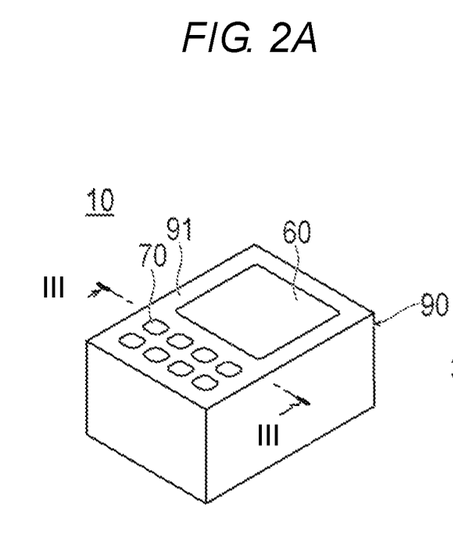
FIG. 2A is a perspective view illustrating a display side of the cardiac function measuring apparatus.
Figure 2B:
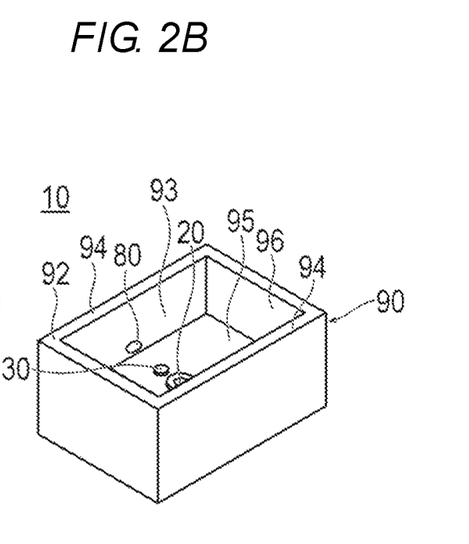
FIG. 2B is a perspective view illustrating a measurement surface side of the cardiac function measuring apparatus.
Figure 3:
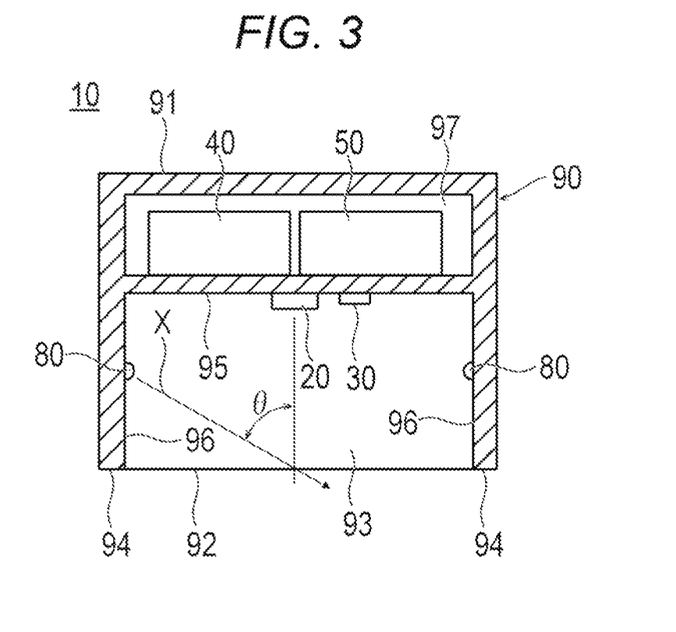
FIG. 3 is a cross-sectional view taken along III-Ill line in FIG. 2A.

The housing 90 includes an operating surface 91 and a measuring surface 92. The display unit 60 and the input unit 70 are disposed on the operating surface 91, and the imaging unit 20, the brightness detection unit 30, and the irradiation unit 80 are disposed on the measuring surface 92. The measuring surface 92 of the housing 90 includes a recessed portion 93. The imaging unit 20, the brightness detection unit 30, and the irradiation unit 80 are disposed in the recessed portion 93. An edge portion surrounding the recessed portion 93 is provided with a supporting portion 94 that comes into contact with a jugular during measurement and supports the housing 90 on the jugular. The recessed portion 93 includes a bottom surface 95 and a side surface 96 surrounding the bottom surface 95. A space 97 is provided between the operating surface 91 and the bottom surface 95 of the housing 90, and the memory unit 40 and the control unit 50 are housed in the space 97.

The imaging unit 20 is an image sensor configured to acquire image data of a jugular for observing expansion of a jugular vein A in the jugular from a body surface. The imaging unit 20 transmits the detected image data to the control unit 50. The imaging unit 20 is disposed at a center portion of the bottom surface 95 of the housing 90, and faces an opening of the recessed portion 93. An imaging direction that the imaging unit 20 faces is preferably vertical to the measuring surface 92 (a surface including the supporting portion 94) in such a way as to be vertical to the body surface in the jugular in contact with the supporting portion 94. A distance from the imaging unit 20 to the measuring surface 92 (the distance to a subject to be imaged) is not specifically limited, but may be, for example, 5 mm to 10 mm. The distance from the imaging unit 20 to the measuring surface 92 is preferably set depending on a view angle of the imaging unit 20 and a size of an area of the measuring surface 92 that is being imaged by the medical personnel.

The brightness detection unit 30 is a brightness sensor configured to detect brightness of an imaging environment. The brightness detection unit 30 transmits the detected brightness data to the control unit 50. The brightness detection unit 30 is disposed on the bottom surface 95 at a position adjacent to the brightness detection unit 30. Any position that allows detection of brightness of the imaging environment may be employed for the brightness detection unit 30.

The irradiation unit 80 is a light source configured to irradiate a subject with light and may be, for example, a Light Emitting Diode (LED). Brightness of the irradiation unit 80 may be adjusted by a brightness adjusting part 51 of the control unit 50. The irradiation unit 80 irradiates a subject to be imaged located on an extension plane of the measuring surface 92 and in front of the imaging unit 20 with light with inclination. The irradiation unit 80 creates a shadow portion S (see FIG. 6) on a far side of a protruded portion on a body surface in a direction of irradiation X. Therefore, the irradiation unit 80 contributes to relatively easy detection of the jugular vein A by the imaging unit 20. Preferably, the direction of irradiation X of the irradiation unit 80 is substantially orthogonal to the jugular vein A, that is, a subject to be measured, in order to create a shadow along a longitudinal direction of the jugular vein A. An angle θ of the direction of irradiation X with respect to the imaging direction (a direction that the irradiation unit 80 faces) is in a range between more than 0 degrees and less than 90 degrees, preferably a range between more than 0 degrees and 83 degrees, and more preferably between 78 degrees and 83 degrees in order to create a shadow in a protruding portion of a body surface.

In the present exemplary embodiment, one (irradiation unit 80) each, two in total, of the irradiation units 80 are disposed on the side surfaces 96 on both sides of the imaging unit 20. Angles 8 of the respective irradiation units 80 may be or may not be the same. The number of the irradiation units 80 is not limited, and one or three or more of the irradiation units 80 may be provided.

Figure 1:
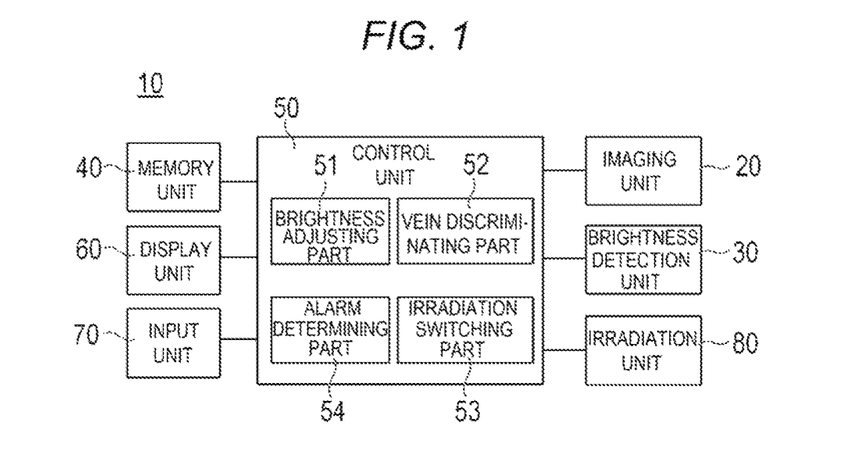
FIG. 1 is a block diagram illustrating a cardiac function measuring apparatus according to an exemplary embodiment.

The memory unit 40 stores various operation programs such as a measuring program executed by the control unit 50 and various parameters (threshold values). The memory unit 40 further stores data detected by the imaging unit 20 and the brightness detection unit 30 and data calculated by the control unit 50.

The control unit 50 includes a brightness adjusting part (brightness adjusting unit) 51, a vein discriminating part (vein discriminating unit) 52, an irradiation switching part (irradiation switching unit) 53, and an alarm determining part (alarm determining unit) 54. The control unit 50 includes a Central Processing Unit (CPU) and an operation program. The control unit 50 integrally controls operations of the imaging unit 20, the brightness detection unit 30, the memory unit 40, the brightness adjusting part 51, the vein discriminating part 52, the irradiation switching part 53, the alarm determining part 54, the input unit 70, the irradiation units 80 and the display unit 60.

The brightness adjusting part 51 acquires brightness data from the brightness detection unit 30. The brightness adjusting part 51 uses the acquired brightness data as well to calculate conditions (output) of the irradiation units 80 for achieving a preset target value in brightness. The brightness adjusting part 51 then controls the irradiation units 80 under the calculated conditions and sets the brightness to the target value.

The vein discriminating part 52 acquires image data from the imaging unit 20. The vein discriminating part 52 calculates a shape complexity level V indicating complexity in shape of the jugular vein A from the image data by a preset method.

Figure 5:
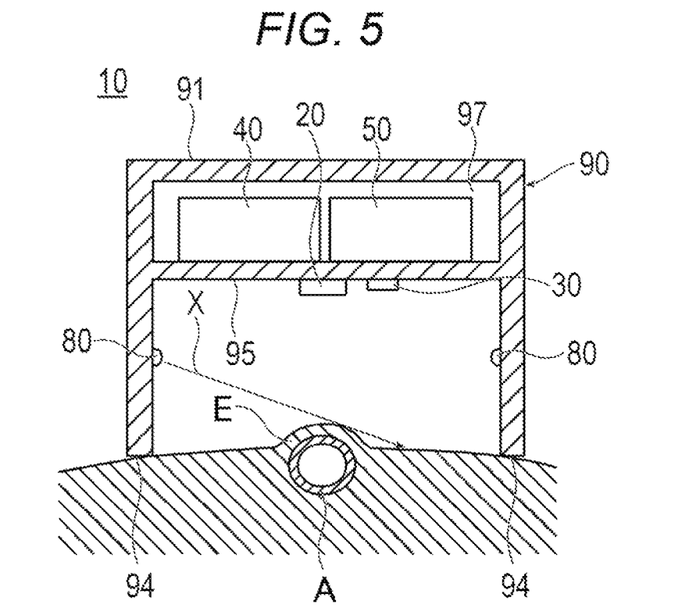
FIG. 5 is a cross-sectional view illustrating the cardiac function measuring apparatus brought into contact with a person being measured.
Figure 6:
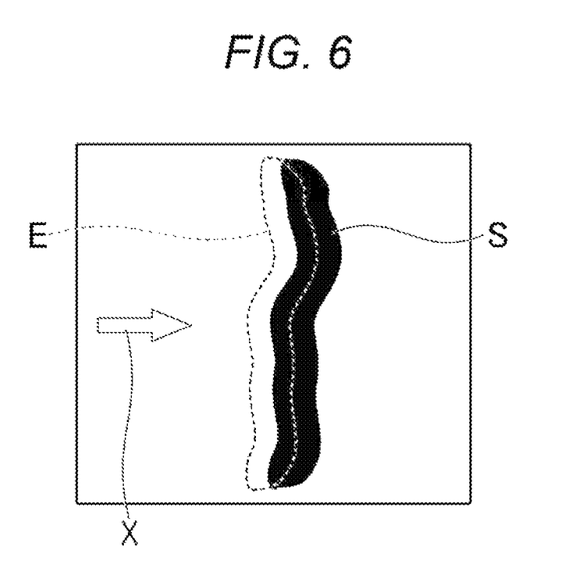
FIG. 6 is a drawing illustrating image data acquired by an imaging unit.
Figure 7:
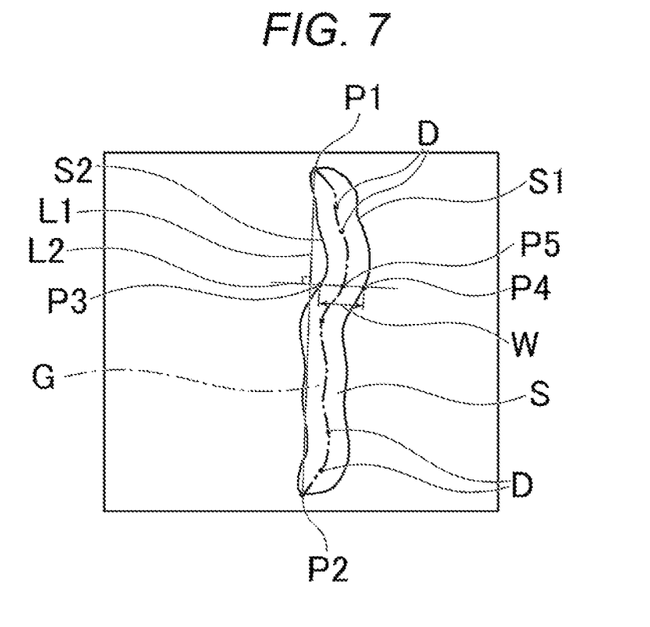
FIG. 7 is a drawing illustrating an external jugular vein determined from the image data acquired by the imaging unit.

An example of calculating the shape complexity level V from the image data will be described. The vein discriminating part 52 classifies tones of respective pixels from the acquired image data. The tones are classified into 256 tones for each of three colors of red, green, and blue, for example. The vein discriminating part 52 then monochromates the image (i.e., the image is contains only one color), and then further posterizes (i.e., the image is displayed using only a small number of different tones) the monochrome image. In the posterization, the vein discriminating part 52 reads a threshold value preset in the memory unit 40, and posterizes into two tones to binarize into black and white. Accordingly, as illustrated in FIGS. 5 and 6, a black shadow portion S appears in a predetermined range on the far side in the direction of irradiation X of a protruding portion E on the body surface. The protruding portion E is formed by expansion of the jugular vein A. The vein discriminating part 52 then calculates a centerline G passing through a center of the shadow portion S as illustrated in FIG. 7. As an example of a method of determining the centerline G, the vein discriminating part 52 determines pixels P1 and P2 of the determined shadow portion S at the farthest positions from each other. The vein discriminating part 52 then determines an orthogonal line L2 orthogonal to a line L1 connecting the pixel P1 and the pixel P2. The vein discriminating part 52 then determines an orthogonal line L2 and edge portions S1 and S2 extending from the pixel P1 to the pixel P2 along an edge of the shadow portion S. The vein discriminating part 52 then determines intersections P3 and P4 between the orthogonal line L2 and the edge portions S1 and S2. The vein discriminating part 52 determines a center point P5 located in the intermediary between the intersection point P3 and the intersection point P4. The vein discriminating part 52 moves the orthogonal line L2 between the pixel P1 and the pixel P2, and determines and arranges center points P5 of the orthogonal line L2 at each point of movement. Accordingly, the vein discriminating part 52 is capable of determining the centerline G formed by arranging the center points P5. The method of calculating the centerline G is not limited to the method described above.

The vein discriminating part 52 then calculates a regression curve of the centerline G, which removes minute fluctuation components from the centerline G to make the centerline G a smooth curve. The vein discriminating part 52 then calculates the number of inflection points D of the regression curve. The vein discriminating part 52 sets a point of the regression curve, where a twice differentiated value is zero (where the inclination of the curve becomes zero), as an inflection point D, and determines the shape complexity level V as the number of the inflection points D. The larger the shape complexity level V, the more complex shape the jugular vein A has. In other words, the external jugular vein A expanded due to deterioration of cardiac functions is more likely to become tortuous and thus become complex. Therefore, the vein discriminating part 52 may determine the number of inflection points D indicating the complexity level of tortuous vein to be the shape complexity level V indicating the complexity in shape of the external jugular vein A.

Any method of calculating the shape complexity level V capable of indicating complexity in shape of the external jugular vein A may be employed. For example, the method of calculating the shape complexity level V may determine the shape complexity level V as the number of times of intersection between the line L1 connecting the pixel P1 and the pixel P2 at the locations farthest from each other and the centerline G. The method of calculating the shape complexity level V may determine the shape complexity level V as a value obtained by dividing the length between the pixel P1 and the pixel P2 at the farthest locations from each other along the centerline G by a direct distance between the pixel P1 and the pixel P2. In the example described above, the method of calculating the shape complexity level V employs calculation of the shape complexity level V by using the shadow portion S. However, the shape complexity level V may be calculated by using a range with intense white color appearing the near side in the direction of irradiation X of the protruding portion E protruding due to expansion of the jugular vein A. The method of calculating the shape complexity level V may also calculate the shape complexity level V in the same manner as the method of calculating from the shadow portion S by binarizing the image data and determining the white range described above. In addition, since the external jugular vein A is different in color from a periphery on the body surface, the method of calculating the shape complexity level V may determine the shape of the external jugular vein A from the shape of the range having different color in the acquired image data.

The method of calculating the shape complexity level V may determine the shape complexity level V as a fluctuation in width W, which corresponds to a distance between the intersection P3 and the intersection P4 between the orthogonal line L2 and the edge portions S1 and S2. In this case, the vein discriminating part 52 calculates the widths W at predetermined intervals from the pixel P1 to the pixel P2. The vein discriminating part 52 may determine the shape complexity level V, for example, as a distribution of a plurality of widths W, a maximum value of the width W, a difference between the maximum value of the width W, or the average value of the widths W.

The vein discriminating part 52 may also determine the shape complexity level V as the average value of a plurality of the shape complexity levels V calculated by using a plurality of the irradiation units 80. By using the average value of the shape complexity level V, complexity in shape may be identified with a relative high degree of accuracy. Instead of the average value, a value providing the best condition may be selected from the plurality of shape complexity levels V calculated for the plurality of irradiation units 80.

The irradiation switching part 53 may select one of the two irradiation units 80 as the irradiation unit 80 to irradiate with light and switch to the selected irradiation unit 80. In response to the start of measurement, the irradiation switching part 53 transmits a signal to the preset irradiation unit 80 and make the corresponding irradiation unit 80 irradiate a subject with light. The irradiation switching part 53 stops irradiation of light upon reception of information indicating that calculation of the shape complexity level V has been terminated from the vein discriminating part 52. After the termination of irradiation of light from the one irradiation unit 80, the irradiation switching part 53 makes the other irradiation unit 80 irradiate a subject with light. The irradiation switching part 53 stops irradiation after the completion of irradiation by all the irradiation units 80.

The alarm determining part 54 compares the shape complexity level V with a threshold value. The threshold value is preset and stored in advance in the memory unit 40, or is input via the input unit 70, or is calculated from data in the past. The alarm determining part 54 determines the presence of abnormality in the cardiac functions if the shape complexity level V exceeds the threshold value. The alarm determining part 54 determines that the cardiac functions are normal if the shape complexity level V does not exceed the threshold value. The alarm determining part 54 causes the display unit 60 to display a result of the determination when the presence of abnormality in the cardiac functions is determined. The threshold value of the alarm determining part 54 may be, for example, an upper limit value of average values of general people, or may be a value of an average value of the person being measured in past several months multiplied by a coefficient.

The input unit 70 is a portion used by the person being measured for an input operation. The input unit 70 may include, for example, a switch, a button, and the like. A touch panel, a keyboard, or a mouse, for example, may also be applicable as the input unit. The input unit 70 is used for inputting or resetting various parameters such as the threshold value, starting and ending measurement, selecting a result to be displayed such as a measurement result and a calculated result, and selecting a graph or a table to be displayed.

The display unit 60 is, for example, a display device such as a Liquid Crystal Display (LCD), or an organic Electro-Luminescence (EL) display. The display unit 60 may be a touch panel that works also as the input unit 70. The display unit 60 may display values that are input via the input unit 70, results of measurement, results of calculation, and results of determination in the form of characters, values, tables, or graphs.

Figure 8:
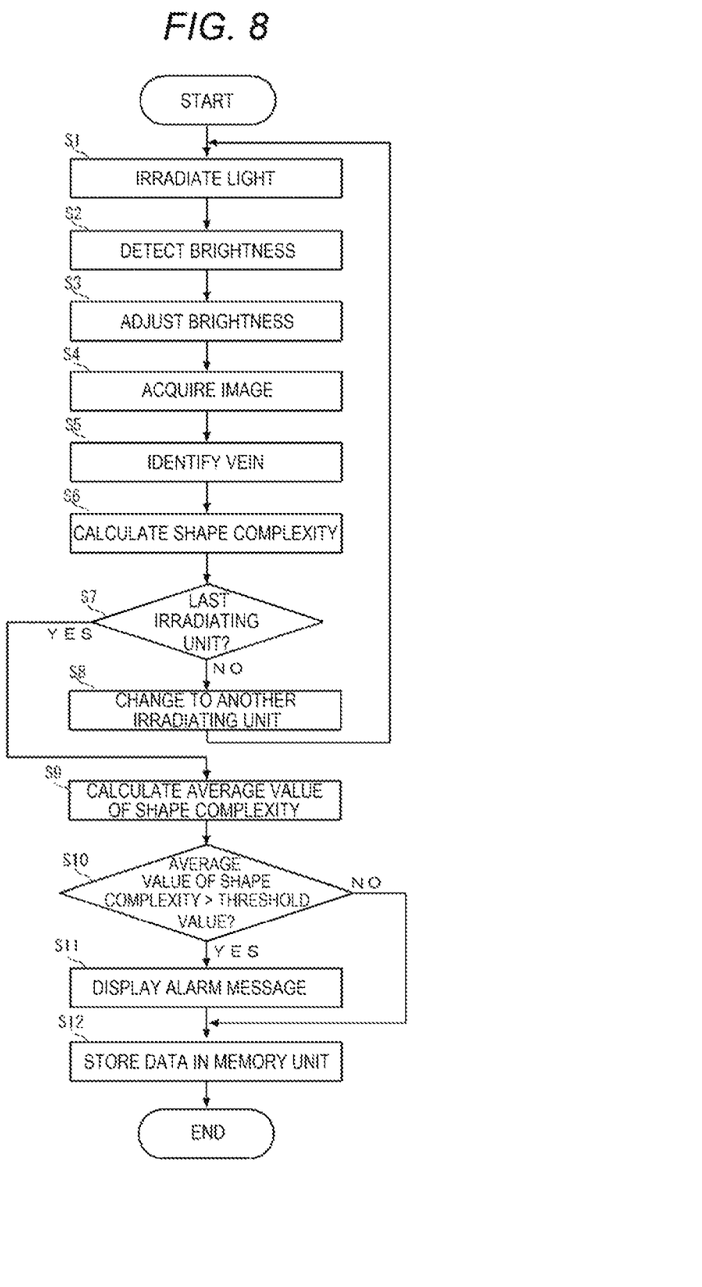
FIG. 8 is a flowchart illustrating a flow of control of the cardiac function measuring apparatus.

A measuring method using the cardiac function measuring apparatus 10 according to the present exemplary embodiment will be described below with reference to a flowchart illustrated in FIG. 8.

Figure 4:
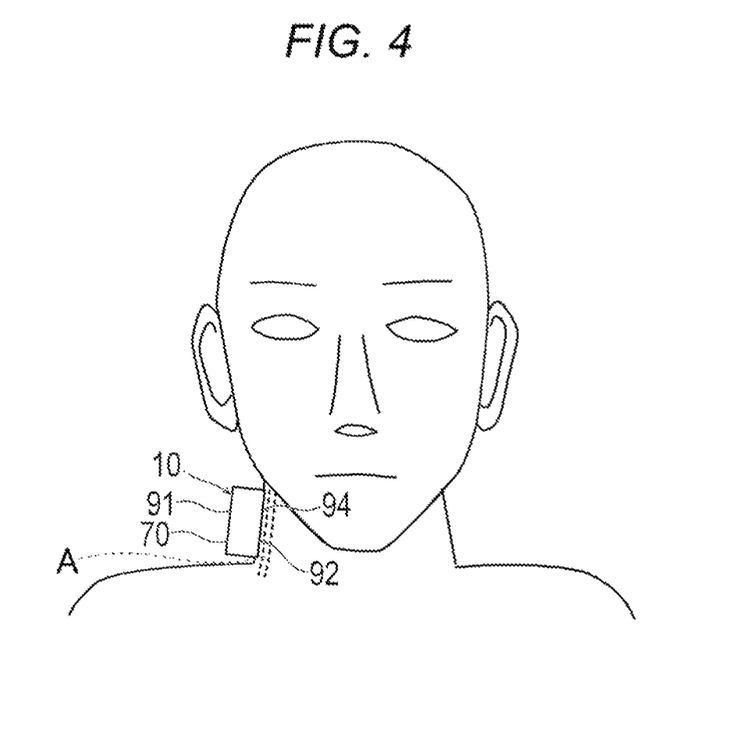
FIG. 4 is a plan view illustrating the cardiac function measuring apparatus brought into contact with a person being measured.

The person being measured brings the supporting portion 94 of the measuring surface 92 of the cardiac function measuring apparatus 10 into contact with the body surface near the jugular vein A as illustrated in FIGS. 4 and 5. At this time, the jugular vein A is positioned in front (i.e., in line with the imaging unit 20) of the imaging unit 20. In order to create the shadow portion S as desired, the direction of irradiation X of the irradiation unit 80 is brought to be as close as possible to be arranged in a direction orthogonal to the jugular vein A. The position of the body surface of the subject and the cardiac function measuring apparatus 10 in contact with the body surface is preferably always the same.

The person being measured operates the input unit 70 of the housing 90 to start measurement. Accordingly, the irradiation switching part 53 transmits an instruction to a predetermined first irradiation unit 80 to cause the corresponding irradiation unit 80 to irradiate a subject with light (Step 1).

Next, the brightness adjusting part 51 receives brightness data from the brightness detection unit 30 (Step 2). The brightness adjusting part 51 calculates conditions (output) of the irradiation units 80 for achieving a preset target value of brightness from the received brightness data. Subsequently, the brightness adjusting part 51 transmits a signal to the irradiation units 80 to achieve the calculated conditions and sets the brightness to the target value (Step 3). Accordingly, the brightness of the imaging environment may be kept constant.

The vein discriminating part 52 then receives the image data from the imaging unit 20 (Step 4). The vein discriminating part 52 then determines the shadow portion S of the protruding portion E on the body surface protruding due to the jugular vein A as illustrated in FIG. 6 (Step 5). Subsequently, the vein discriminating part 52 calculates the shape complexity level V from information on the determined shadow portion S (Step 6).

After completion of calculation of the shape complexity level V in the vein discriminating part 52, the vein discriminating part 52 transmits information indicating the completion of the calculation to the irradiation switching part 53. The irradiation switching part 53 that has received the information then discriminates whether the irradiation unit 80 in operation is the last irradiation unit 80 or not (Step 7). If the irradiation unit 80 in operation is not the last irradiation unit 80, the irradiation switching part 53 transmits an instruction to the irradiation unit 80 in operation to stop irradiation of light and transmits an instruction to the other irradiation unit 80 to cause the other irradiation unit 80 to irradiate the subject with light (Step 8).

Subsequently, Step 1 to Step 6 described above are repeated and the second shape complexity level V is calculated by using the second irradiation unit 80.

After completion of calculation of the second shape complexity level V in the vein discriminating part 52, the vein discriminating part 52 transmits information indicating the completion of calculation to the irradiation switching part 53. The irradiation switching part 53 that has received the information then discriminates whether the irradiation unit 80 in operation is the last irradiation unit 80 or not (Step 7). If the irradiation unit 80 in operation is the last irradiation unit 80, the irradiation switching part 53 transmits an instruction to the irradiation unit 80 in operation to stop irradiation of light. Subsequently, the vein discriminating part 52 calculates an average value of the shape complexity level V calculated respectively by the plurality of irradiation units 80 (Step 9).

Figure 9:
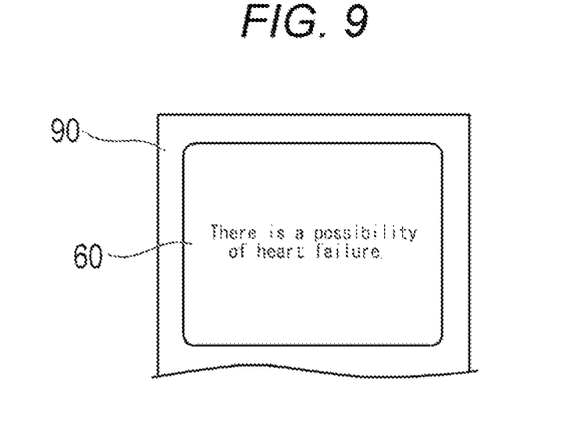
FIG. 9 is a plan view illustrating a display unit displaying an alarm message.

The alarm determining part 54 then compares the average value of the shape complexity level V with the threshold value. Accordingly, the alarm determining part 54 determines whether the average value of the shape complexity levels V is normal or not (Step 10). When the average value of the shape complexity levels V is determined to be abnormal, the alarm determining part 54 displays an alarm message in the display unit 60 as illustrated in FIG. 9 (Step 11). The content of the alarm message may be set as needed.

Figure 10:
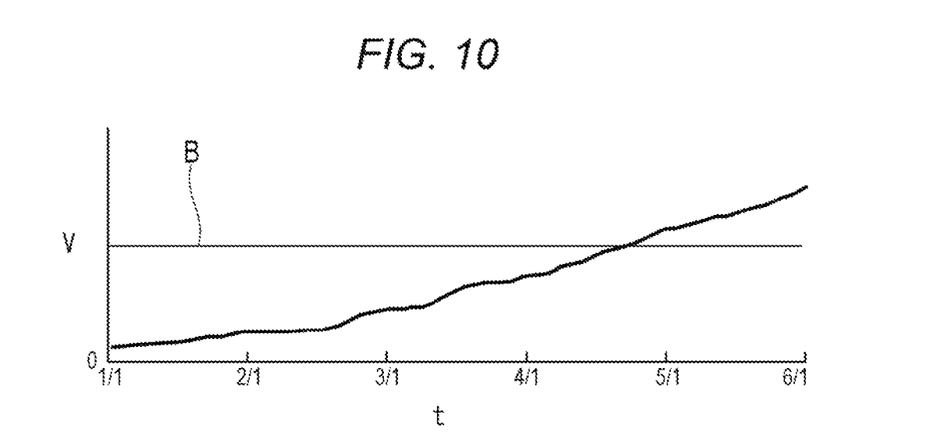
FIG. 10 is a graph illustrating a change in shape complexity level by the day calculated by the cardiac function measuring apparatus.

The control unit 50 is capable of causing the display unit 60 to display variations in average value of the shape complexity levels V at each time of measurement together with data in the past with time (t) on an abscissa axis as illustrated in FIG. 10. The control unit 50 is capable of displaying an upper limit B (threshold value) of the normal value of the shape complexity level V with a line on the graph to be displayed in the display unit 60. In this graph, when the shape complexity level V exceeds the upper limit B, it may be determined that a flowing route of the jugular vein A is bent by the blood pressure, and thus cardiac arrest has occurred or cardiac arrest may occur. Therefore, the person being measured him/herself can rather easily monitor the extent of progression of cardiac arrest (deterioration of cardiac functions) for a relatively long term.

Subsequently, the control unit 50 causes the memory unit 40 to store data such as the calculated shape complexity levels V and the presence or absence of abnormality (Step 12). Accordingly, the measurement to be performed by the cardiac function measuring apparatus 10 is completed. The measurement by the cardiac function measuring apparatus 10 can be performed, for example, every day (i.e., daily). Accordingly, the cardiac functions of the person (or subject) may be monitored for a relatively long term. The measurement does not have to be performed every day.

As described thus far, the cardiac function measuring apparatus 10 according to the present exemplary embodiment is an apparatus for measuring data for evaluating cardiac functions, and includes the irradiation units 80 for irradiating the jugular with light, the imaging unit 20 configured to acquire image data of the jugular, and the vein discriminating part 52 configured to determine the shape of the jugular vein A in the acquired image data and calculate the shape complexity level V indicating complexity in the shape.

The cardiac function measuring apparatus 10 as described above may calculate the shape complexity level V indicating complexity in shape of the jugular vein A by using the image data of the jugular created by light irradiated from the irradiation unit 80. Accordingly, the complexity in shape of the jugular vein A as an indication of deterioration of cardiac functions may be monitored by the shape complexity level V, and thus monitoring of the cardiac functions can be facilitated. In addition, the cardiac function measuring apparatus 10 may have a compact size and provide a relative easy-to-measure configuration, and may achieve relatively long-term monitoring with rather less burden to a person being measured.

The cardiac function measuring apparatus 10 further includes the memory unit 40 capable of storing the shape complexity levels V, and is capable of comparing the shape complexity levels V measured and calculated at each different times. Accordingly, variations of cardiac functions with time may be observed, and thus the cardiac functions may be monitored rather easily for a long term.

The vein discriminating part 52 may calculate the centerline G (line) along the shape of the discriminated jugular vein A, calculate the regression curve of the centerline G, and determine the shape complexity level V as the number of the inflection points D of the regression curve. Accordingly, the shape complexity level V as the indication of deterioration of cardiac functions may be calculated from the shape of the jugular vein A rather easily with a relative high degree of accuracy. The line along the shape of the jugular vein A is not limited to the centerline G and may be lines (edge portions S1 and S2) along an edge of the discriminated jugular vein A as long as the line expresses characteristics of the jugular vein A.

The cardiac function measuring apparatus 10 further includes the alarm determining part 54 configured to compare the calculated shape complexity level V with the threshold value and determines whether an alarm is to be issued or not. Accordingly, determination of the cardiac functions can be performed automatically, and thus determination of the deterioration of cardiac functions is achieved rather easily.

The cardiac function measuring apparatus 10 further includes the brightness detection unit 30 configured to detect brightness, the brightness adjusting part 51 configured to adjust the irradiation units 80 to bring the brightness to be detected by the brightness detection unit 30 closer to the target value. Accordingly, since the brightness of the imaging environment may be set adequately at each time of measurement, the imaging conditions at every measurement may be equalized, and thus monitoring of cardiac functions with a relative high degree of accuracy can be achieved.

The cardiac function measuring apparatus 10 further includes the supporting portion 94 located at a position in the imaging direction with respect to the imaging unit 20 and capable of coming into contact with the jugular. Accordingly, the distance from the imaging unit 20 to the jugular may be set adequately by bringing the supporting portion 94 into contact with the jugular at each time of measurement. Therefore, the imaging conditions at every measurement become uniform and monitoring of cardiac functions with a relatively high degree of accuracy can be achieved.

The disclosure also includes a cardiac function measuring method for measuring data for evaluation of cardiac functions. The cardiac function measuring method includes: irradiating a jugular with light; acquiring image data of the jugular irradiated with light; discriminating a shape of a jugular vein A in the image data acquired; and calculating a shape complexity level V indicating complexity in shape of the jugular vein A discriminated.

The cardiac function measuring method as described above may calculate the shape complexity level V indicating the complexity in shape of the jugular vein A by using the image data of the jugular created by light irradiated from the irradiation unit 80. Accordingly, the complexity in shape of the jugular vein A as an indication of deterioration of cardiac functions may be monitored by the shape complexity level V, and thus monitoring of the cardiac functions is facilitated. In addition, since the cardiac function measuring apparatus 10 provides an easy-to-measure configuration, long-term monitoring with relatively less burden imposed to a person being measured can be achieved.

The cardiac function measuring method further includes comparing the shape complexity levels V measured and calculated at different times. Accordingly, variations of cardiac functions with time may be observed, and thus the cardiac functions may be monitored rather easily for a relatively long term.

Calculating the shape complexity level V of the cardiac function measuring method may include calculating the centerline G (line) along the shape of the discriminated jugular vein A, calculating the regression curve of the centerline G, and determining the shape complexity level V as the number of the inflection points D of the regression curve. Accordingly, the shape complexity level V as the indication of deterioration of cardiac functions may be calculated from the shape of the jugular vein A rather easily with a relative high degree of accuracy.

The cardiac function measuring method further includes comparing the calculated shape complexity level V with the threshold value and determining whether an alarm is to be issued or not. Accordingly, determination of the cardiac functions is performed automatically, and thus determination of the deterioration of cardiac functions is achieved rather easily.

The disclosure also includes a cardiac function measuring program to be executed by a computer for measuring data for evaluation of cardiac functions. The cardiac function measuring program includes: acquiring image data of a jugular from the imaging unit 20 capable of imaging the jugular; discriminating a shape of a jugular vein A in the image data acquired; and calculating shape complexity level V indicating complexity in shape of the jugular vein A discriminated.

The cardiac function measuring program as described above may calculate the shape complexity level V indicating the complexity in shape of the jugular vein A by using the image data of the jugular created by light irradiated from the irradiation unit 80. Accordingly, the complexity in shape of the jugular vein A as an indication of deterioration of cardiac functions may be observed by the shape complexity level V, and thus monitoring of the cardiac functions can be facilitated (or performed). In addition, since the cardiac function measuring apparatus 10 provides a rather easy-to-measure configuration, long-term monitoring with relatively less burden to a person being measured can be achieved.

The cardiac function measuring program further includes reading the shape complexity levels V measured and calculated at different times from the memory unit and comparing the plurality of shape complexity levels V measured at different times. Accordingly, variations of cardiac functions with time may be observed, and thus the cardiac functions may be monitored rather easily for a relatively long term.

Calculating the shape complexity level V of the cardiac function measuring program may include calculating a centerline G (line) along the shape of the discriminated jugular vein A, calculating the regression curve of the centerline G, and determining the shape complexity level V as the number of the inflection points D of the regression curve. Accordingly, the shape complexity level V as the indication of deterioration of cardiac functions may be calculated from the shape of the jugular vein A rather easily with a relative high degree of accuracy.

The cardiac function measuring program further includes comparing the calculated shape complexity level V with the preset threshold value and determining whether an alarm is to be issued or not. Accordingly, determination of the cardiac functions is performed automatically, and thus determination of the deterioration of cardiac functions can be achieved rather easily.

Note that the present disclosure is not limited only to the exemplary embodiments described above, and various modifications may be made by skills in the art within a technical scope of the present disclosure. For example, the configuration of the housing is not specifically limited. At least part of functions of the cardiac function measuring apparatus may be configured with mobile terminals and an application (program) such as smart phones or tablet terminals, or server computer terminals connected to internet and application (program). In this case, the part of functions may be connected, for example, to portable terminals over the wireless by using a communication technique such as Near Field Communication (NFC) or Wi-Fi (registered trademark). The cardiac function measuring apparatus 10 is configured on the assumption of being used by the person being measured. However, the cardiac function measuring apparatus 10 may be used by medical personnel including doctors and nurses for the person being measured.

External jugular veins can be observed rather easily through the body surface, while internal jugular veins are located at a deep part of the body. Therefore, the internal jugular veins may not be observed through the body surface with a general image sensor (imaging device). Therefore, in order to observe internal jugular veins, the imaging unit is preferably configured to be capable of observing the deep part of the body. The imaging unit capable of observing the deep part of the body utilizes an ultrasound probe using ultrasound wave echo, an Optical Coherence Tomography (OCT), and an Optical Frequency Domain Imaging (OFDI). The imaging unit capable of observing the deep part of the body may be a device capable of identifying the shape of the jugular vein by measuring the sound of pulsation of the jugular vein at a plurality of positions on the body surface and determining the shape of the jugular vein from the sound intensities of the pulsation at the respective positions of measurement. The cardiac function measuring apparatus, the cardiac function measuring method, and the cardiac function measuring program may be configured by using the imaging unit capable of observing the deep part of the body as described above.

The detailed description above describes a cardiac function measuring apparatus, a cardiac function measuring method, and a cardiac function measuring program configured to measure data for evaluating cardiac functions. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A cardiac function measuring apparatus configured to measure data for evaluating cardiac functions of a user, comprising:
an irradiator configured to irradiate a jugular with light;
an imager configured to acquire image data of the jugular;
a vein discriminator configured to:
discriminate a shape of a jugular vein in the acquired image data; and
calculate a shape complexity level of the jugular vein, the shape complexity level indicating complexity in the shape of the jugular vein; and
an alarm determining unit configured to:
compare the shape complexity level of the jugular vein to a threshold value of complexity levels of the jugular vein; and
evaluate the shape of the jugular vein for a change in a cardiac status of the user based on the comparison of the shape complexity level of the jugular vein to the threshold value of complexity levels of the jugular vein.

2. The cardiac function measuring apparatus according to claim 1, further comprising:
a memory configured to store a plurality of shape complexity levels of the jugular vein of the user; and
wherein the cardiac function measuring apparatus is configured to compare the plurality of shape complexity levels acquired at different times.

3. The cardiac function measuring apparatus according to claim 1, wherein the vein discriminator is configured to calculate a line in conformance with the shape of the discriminated jugular vein, calculate a regression curve of the line, and determine the shape complexity level as a number of inflection points of the regression curve.

4. The cardiac function measuring apparatus according to claim 1, further comprising:

a display configured to display a result when a presence of an abnormality in the cardiac functions of the user is determined.

5. The cardiac function measuring apparatus according to claim 1, further comprising:
an input device configured to input parameters of the cardiac function measuring apparatus, the parameters of the cardiac function measuring apparatus including one or more of the threshold value of complexity levels of the jugular vein, starting and ending measurements, and a selection of a result to be displayed on the display, the result including one or more of a measurement result, a calculated result, a graph, and a table.

6. The cardiac function measuring apparatus according to claim 1, further comprising:
a brightness detector configured to detect brightness of an imaging environment; and
a brightness adjustor configured to adjust the irradiation irradiator to bring the detected brightness from the brightness detector to a target value.

7. The cardiac function measuring apparatus according to claim 1, wherein the alarm determining unit is configured to:
determine a presence of an abnormality in the cardiac functions of the user when the shape complexity level exceeds the threshold value, and determine that the cardiac functions of the user are normal when the shape complexity level does not exceed the threshold value.

8. The cardiac function measuring apparatus according to claim 1, further comprising:
a housing configured to house the irradiator, the imager, the vein discriminator, a brightness detector, a memory, a controller, an input device, and a display, and wherein the housing includes an operating surface and a measuring surface, the display and the input device being disposed on the operating surface, and the imager, the brightness detector, and the irradiator being disposed on the measuring surface;

the measuring surface of the housing including a recessed portion, the imager, the brightness detector, and the irradiator being disposed in the recessed portion;

an edge portion surrounding the recessed portion having a supporting portion configured to come into contact with the jugular during measurement and configured to support the housing on the jugular; and wherein the recessed portion includes a bottom surface and a side surface surrounding the bottom surface, and a space being provided between the operating surface and the bottom surface of the housing, and wherein the memory and the controller are housed in the space.

9. The cardiac function measuring apparatus according to claim 8, wherein the irradiator comprises two irradiators, the two irradiators being disposed on the side surface of the housing, and wherein the two irradiator are on opposite sides of the imager.

10. The cardiac function measuring apparatus according to claim 1, wherein the threshold value of complexity levels of the jugular vein is an average value of complexity levels of the jugular vein of the user being evaluated for the change in the cardiac status multiplied by a coefficient.

* * * * *